(12) United States Patent
Yu et al.

(10) Patent No.: US 9,567,611 B2
(45) Date of Patent: Feb. 14, 2017

(54) TWO-STAGE ANAEROBIC DIGESTION SYSTEMS WHEREIN ONE OF THE STAGES COMPRISES A TWO-PHASE SYSTEM

(71) Applicant: Washington State University, Pullman, WA (US)

(72) Inventors: Liang Yu, Pullman, WA (US); Jingwei Ma, Pullman, WA (US); Craig Frear, Pullman, WA (US); Usama Zaher, Pullman, WA (US); Shulin Chen, Pullman, WA (US)

(73) Assignee: Washington State University, Pullman, WA (US)

( * ) Notice: Subject to any disclaimer, the term of this patent is extended or adjusted under 35 U.S.C. 154(b) by 175 days.

(21) Appl. No.: 14/522,075

(22) Filed: Oct. 23, 2014

(65) Prior Publication Data

US 2015/0056676 A1 Feb. 26, 2015

Related U.S. Application Data

(63) Continuation of application No. 13/673,273, filed on Nov. 9, 2012, now abandoned.

(60) Provisional application No. 61/563,012, filed on Nov. 22, 2011.

(51) Int. Cl.
| | |
|---|---|
| *C12P 5/02* | (2006.01) |
| *C12M 1/107* | (2006.01) |
| *C12M 1/00* | (2006.01) |
| *C12M 1/34* | (2006.01) |

(52) U.S. Cl.
CPC ............... *C12P 5/023* (2013.01); *C12M 21/04* (2013.01); *C12M 23/58* (2013.01); *C12M 29/18* (2013.01); *C12M 41/26* (2013.01); *Y02E 50/343* (2013.01)

(58) Field of Classification Search
None
See application file for complete search history.

(56) References Cited

U.S. PATENT DOCUMENTS

| | | |
|---|---|---|
| 5,958,756 A | 9/1999 | Reynell |
| 6,551,510 B1 | 4/2003 | Bakke et al. |
| 2007/0158264 A1 | 7/2007 | Zhang |
| 2012/0015430 A1 | 1/2012 | Christensen |

*Primary Examiner* — Karen Cochrane Carlson
*Assistant Examiner* — Jennifer M. H. Tichy
(74) *Attorney, Agent, or Firm* — Whitham, Curtis & Cook, P.C.

(57) ABSTRACT

Low cost, efficient two-stage anaerobic digestion systems for the production of biogas (e.g. methane) are provided. During the first stage, biogas is produced in a first reactor by anaerobic microbes cultured in two phases: a high solids phase and a low solids phase. During the second stage, biogas is produced in a second reactor by a methanogen-rich anaerobic culture cultured in low solids medium. Removal of effluent comprising pH lowering reaction products assists in maintaining a suitable pH in the high solids phase. The transfer of effluent from the second reactor to the first reactor assists in maintaining a suitable pH in the high solids phase, in mixing of the high solids phase, and in reseeding the high solids phase with methanogens. Methane is produced in and recovered from both reactors.

20 Claims, 9 Drawing Sheets

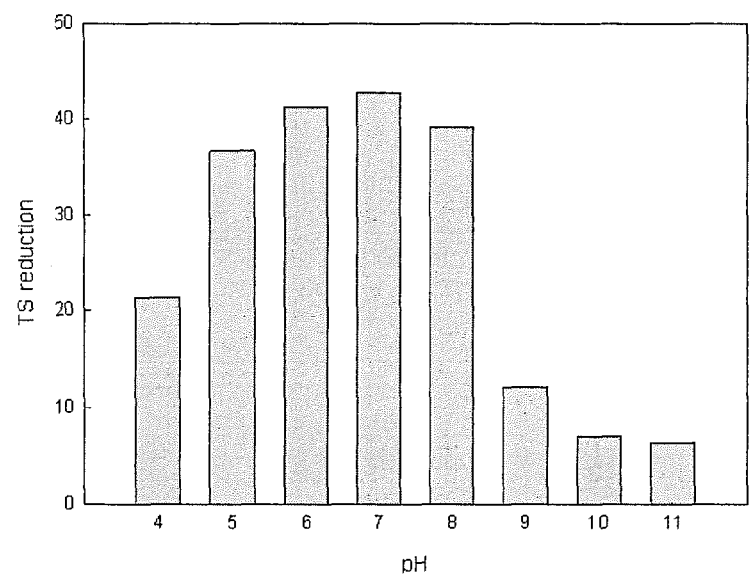
Figure 4
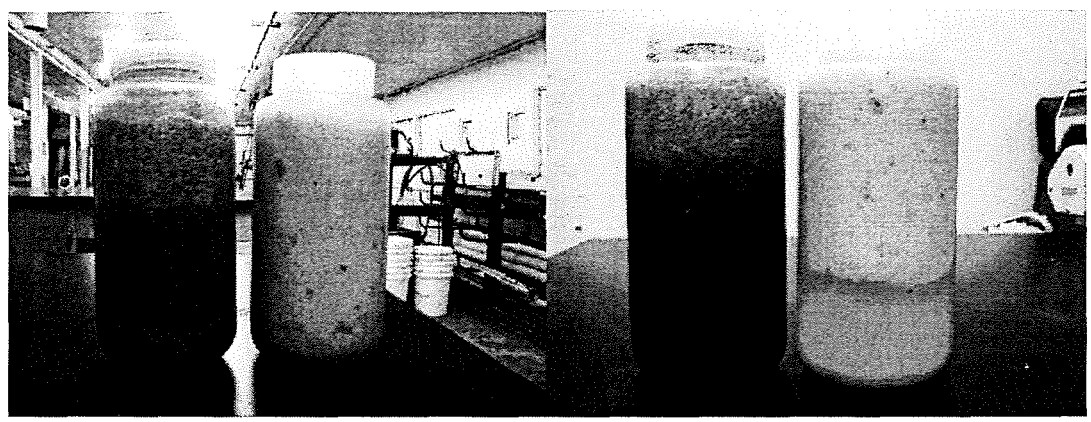
Figure 5A and B

TWO-STAGE ANAEROBIC DIGESTION SYSTEMS WHEREIN ONE OF THE STAGES COMPRISES A TWO-PHASE SYSTEM

FIELD

The invention generally relates to two stage anaerobic digestion systems for the production of biogas. In particular, during the first stage, biogas is produced in a first reactor by one anaerobic microbial consortium cultured in two phases: a high solids phase and a low solids phase, whereas during the second stage, biogas is produced in a second reactor by a methanogen-rich anaerobic culture cultured in low solids medium.

BACKGROUND

Anaerobic digestion is a series of processes in which organic material is dissolved and chemically converted in the absence of oxygen so that it can be absorbed by the cells of an organism and used to maintain biological functions. During anaerobic digestion, complex carbohydrates (e.g., cellulose and starch), lipids, fibers, and proteins, are converted into simpler compounds (e.g. sugars, glycerin and fatty acids, and amino-acids) which can be taken up by cells. Conversion occurs due to reduction of the complex organic compounds by hydrolytic enzymes, such as cellulases, proteases, and lipases, secreted by bacteria, which split the long molecular chains into monomer units.

The process of commercial anaerobic digestion generally employs specialized bacteria to break down organic waste as described above, and then to convert it into biogas (a mixture of carbon dioxide and methane) and a stable biomass. Under anaerobic conditions, a considerable portion of the chemical oxygen demand (COD) is converted to methane gas as an end product. Methane is a potential energy source, and its production from waste considerably lessens waste biomass disposal requirement and the financial burden associated with disposal. Biogas produced from anaerobic digestion has thus been promoted as a part of the solution to energy problems. Methane has a calorific value of 9000 kcal/m$^3$, and can be burned on site or elsewhere, for example, to provide heat for digesters or to generate electricity.

Solid waste and other biodegradable solid substrates should be handled, as much as possible, in a manner that reduces their environmental impact, recovers energy locked therein, and avoids massive disposal treatments (e.g., landfill, incineration, etc.). Most of the anaerobic digestion technologies that are currently applied to domestic wastewater treatment, dairy and swine manure, and food processing waste can handle up to 10% total solids (TS). Application of these existing technologies to process high solids (>10%) streams often require significant dilution, larger digester sizes and high fresh water consumption, resulting in very high capital investment costs. High solids digestion technologies for municipal solid waste treatment have been developed and applied more extensively in Europe than in the US. However, these technologies depend on significant recycling of the treated solids to maintain the bacterial population in the digester, which requires additional reactor volume and expensive equipment.

The treatment of solid waste using anaerobic digestion poses several challenges because of the variety in the feedstock and the space limitations where such facilities can be located. For example, the organic fraction of municipal solid waste (OFMSW) may contain agricultural, food, yard waste, and/or paper in varying concentrations, sizes, and compositions. Furthermore, municipal solid waste is contaminated with non-organics, such as glass and metal, and therefore requires pre-treatment to separate these from the feedstock. Though the ideal waste stream for an anaerobic digestion plant would be source-separated organics, the reality is that there is always a small degree of contamination that must be handled on site, and additional equipment is usually needed to remove this contamination prior to digestion in existing anaerobic digestion systems.

Preferred designs of anaerobic digestion systems reflect the need for shorter hydraulic retention times (HRTs), higher retention of biomass, smaller reactor volumes and higher loading rates, indicative of their urban locations. U.S. Pat. No. 4,735,724 (Chynoweth, et al.) describes a non-mixed vertical tower anaerobic digester for accommodating high solids loadings and providing separation of microbial phases within the continuous digester volume to achieve substantially complete bioconversion of biodegradable feedstock components. Due to the passive concentration of solids in the upper portion of the reactor, biodegradable solids have an increased retention time in the digester, whereas liquids and non-biodegradable components have a reduced retention time, since they migrate to lower portions of the digester and are withdrawn preferentially. Non-mixing allows this single digester to be operated at high solids loading because passive concentration of solids and the separation of microbial phases within a continuous digester volume results in greater system stability. However, overall kinetics of the degradation process and therefore biogas productivity as well as yield is reduced, primarily as a result of the passive mixing and overall high loading.

Separated two-stage anaerobic digestion processes, where the acid stage digestion and the methane stage digestion are carried out in two separate reactor vessels, have been found to enhance the efficiency of conversion of organic carbonaceous materials to methane. The main disadvantage is the cost of such more complex systems. Two-stage anaerobic digestion of organic carbonaceous materials to produce methane is generally taught by U.S. Pat. No. 4,022,665, U.S. Pat. No. 4,318,993, and U.S. Pat. No. 4,696,746 (all to Ghosh, et al). Each of these patents teaches performing acid stage digestion and methane stage digestion in two separate reactor vessels. Each of these patents also teaches operating conditions for acid stage and methane stage digestion. U.S. Pat. No. 5,500,123 (Srivastava) describes operating conditions for a two-stage anaerobic digestion process, such as feed rates and retention times, and teaches introduction of oxygen into the methane phase digester to produce biogas having a methane content in excess of 80%.

U.S. Pat. No. 6,342,378 (Zhang, et al. and U.S. Pat. No. 7,556,737 (Zhang) teaches methods and a device for the generation of methane by a two-stage anaerobic phase system (APS) digestion of organic substrates. The APS-digester system is a space-efficient, high-rate solids digestion system. The APS-digester system consists of one or more hydrolysis reactors and one biogasification reactor. The hydrolysis phase, the buffer tank and the methanogenesis phase are operative over variable pH ranges that are related to the nature of the organic substrate and the amount of total solids in the organic substrate. In a preferred embodiment, the pH of the hydrolysis reactor is maintained in the range of from about 4.5 to about 7.0. In another preferred embodiment, the biogasification stage pH is maintained in the range of from about 6.5 to about 8.0. Compared with the other two-stage systems in U.S. patents, the APS-digester can process higher total solids organic waste streams. The microorganisms in the hydrolysis reactors are selected and environmental conditions are controlled to allow production and release of hydrogen in the first stage prior to methane production in the second stage.

Such prior art two-stage systems are best suited for degrading highly cellulosic feedstock such as rice straw, forestry waste, agricultural waste, and water and land plants or organic carbonaceous material with low total solids such as sewage sludge, municipal waste, and animal waste. If these two-stage systems are applied to easily degradable high solids waste such as food waste or animal waste, the main advantage would be producing relatively high hydrogen gas content in the first step but at the cost of no methane production in the first step and low methane production in the second step. However, current hydrogen production from anaerobic digestion is not economically viable because of the high cost required to purify the hydrogen gas content from 30% to over 98% to meet the hydrogen quality standards such as Title 13 CCR Section 2292.7-1995, JIS K-0512 Type 3 and MIL-PRF-27201C. Furthermore, the previous two-stage systems are either simple but inefficient, or efficient but complicated.

There is a need in the art for simplified, efficient and cost effective anaerobic digester systems for high solids waste streams.

SUMMARY

The anaerobic digesters described herein are two-stage systems wherein one of the two stages comprises a two-phase digester. These systems are designed to provide an enhanced methane output during the digestion of mixtures that contain solid wastes. In some embodiments, the solid waste includes or is the organic fraction of municipal solid wastes (OFMSW). A feature of this system is that the entire system comprises two-stages carried out in two separate reactors with the first stage reactor operating in two-phases. The systems and methods provide enhanced methane productivity and decreased operational costs for anaerobic digestion of high solids mixtures, especially those that contain municipal wastes.

Accordingly, provided herein are methods of producing biogas, comprising the steps of i) in a first reactor, culturing at least one anaerobic microbial consortium in a high solids medium comprising 10 to 20% solids and having a pH in the range of from 6.0 to 7.5, for a period of time sufficient to produce biogas containing methane and to form a high solids phase and a low solids phase within said first reactor. The high solids phase is positioned within a top portion of the first reactor and the low solids phase is positioned within a bottom portion of the first reactor, and the high solids phase and the low solids phase are in direct contact with each other; ii) culturing, in a second reactor, at least one methanogen-rich anaerobic culture in a low solids medium comprising at most 1% solids and having a pH in the range of from 6.5 to 8.5, for a period of time sufficient to generate methane; and, during said steps of i) culturing and ii) culturing, iii) removing effluent containing volatile fatty acids (VFAs) from the low solids phase in the first reactor at a rate that is sufficient to at least partially offset a decrease in pH within the high solids phase; iv) transferring effluent removed from said low solids phase in the first reactor to the second reactor; v) removing effluent from the low solids medium in the second reactor; vi) transferring effluent removed from the second reactor to the first reactor at a rate that is sufficient to at least partially offset the decrease in pH within the high solids phase; and vii) recovering biogas produced in at least one of the first and second reactors. In some embodiments, the method further comprises a step of processing, in a buffer tank, the effluent removed from the first and/or the second reactor prior to the steps of iv) and vi) transferring. In such embodiments, the step of processing may include adjusting a pH of said effluent, e.g. by alkalinization. In other embodiments, the effluent transferred from the low solids medium in the second reactor to the first reactor comprises anaerobic seeds, for example, methanogenic seeds. In some embodiments, the high solids medium comprises organic municipal solid waste. In other embodiments, the steps of i) culturing and ii) culturing are performed simultaneously. In yet other embodiments, the methods further comprise a step of transferring $H_2$ and $CO_2$ produced in the first reactor to the second reactor. In yet other embodiments, the biogas recovered in the recovering step includes methane. In some embodiments, further comprising the step of i) recovering nutrients from the effluent removed from the second reactor prior to the step vi) of transferring. In other embodiments, the methods further comprise the steps of i) transferring effluent from the first reactor and/or the second reactor to a buffer tank; ii) recovering nutrients from the effluent transferred to the buffer tank; and iii) transferring nutrient depleted effluent from the buffer tank to the first reactor. In some embodiments, the methods further comprise a step of mixing the high solids phase. In other embodiments, the step of mixing is performed by a method selected from: i) mechanical mixing; and ii) introducing effluent from the second reactor into the top portion of the first reactor.

Also provided herein is a system for producing biogas from high solids waste. The system comprises: a first reactor; a second reactor; one or more means for transferring liquid from the first reactor to the second reactor; one or more means for transferring liquid from the second reactor to the first reactor; and a controller that uses data concerning one or more of i) conditions in a high solids phase in the first reactor, ii) conditions in a low solids phase in the first reactor, and iii) conditions in a low solids liquid medium in the second reactor; said controller being capable of adjusting a flow of liquid from said first reactor to said second reactor and from said second reactor to said first reactor in response to said data. In some embodiments, the data includes pH values. In other embodiments, the system also comprises a buffer tank, one or more means for transferring liquid: i) from the first reactor to the buffer tank, ii) from the buffer tank to the first reactor, iii) from the second reactor to the buffer tank, and iv) from the buffer tank to the second reactor. In other embodiments, the controller is capable of adjusting a flow of liquid: i) from the first reactor to the buffer tank, ii) from the buffer tank to the first reactor, iii) from the second reactor to the buffer tank, and iv) from the buffer tank to the second reactor, in response to the data. In some embodiments, the system comprises one or more means to transfer gases from the first reactor to the second reactor. In yet other embodiments, the system comprises a means for mixing the high solids phase in the first reactor.

BRIEF DESCRIPTION OF THE DRAWINGS

The above-mentioned and other features and objects of this invention will be better understood from the following detailed description taken in conjunction with the drawings wherein:

FIG. 4 is change in total solids (TS) reductions with pH FIGS. 5A and B. The natural separation of liquid and solid A, the first day, B, the second day).

DETAILED DESCRIPTION

Abbreviations

Figure 1:
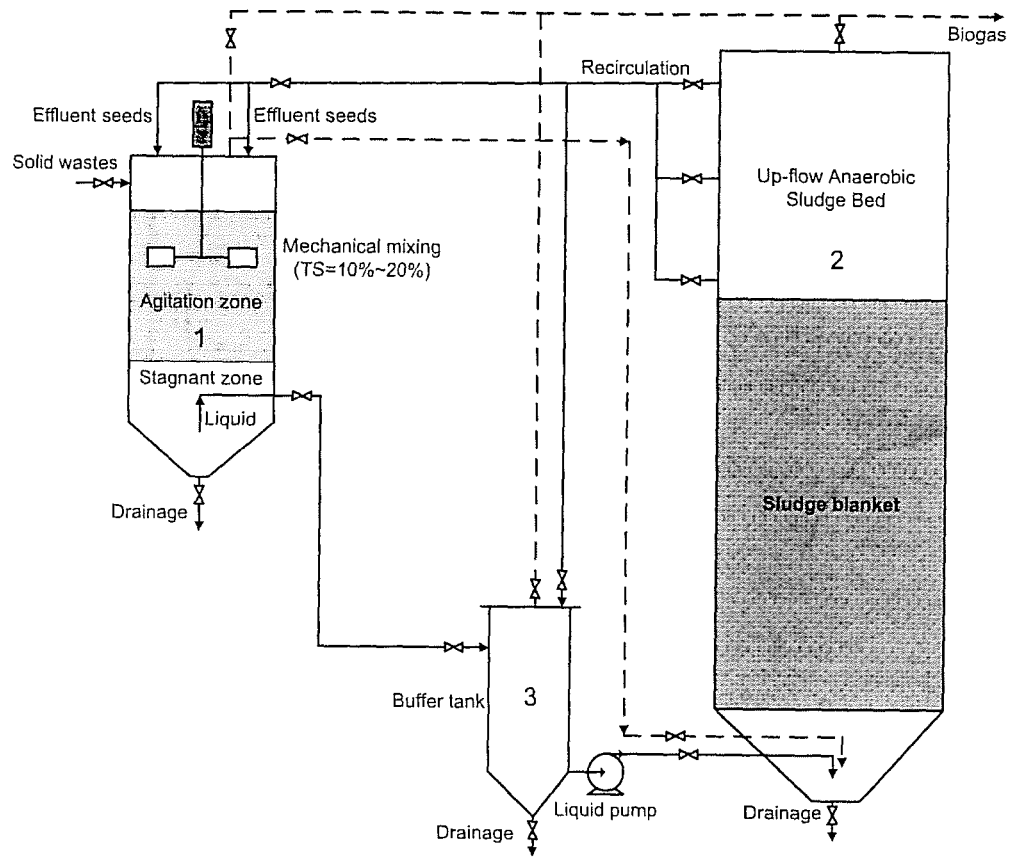
FIG. 1 is a schematic flow diagram of the high-solid anaerobic digester with recycling seeds system (HADRS) system in accordance with one embodiment of this invention.

HADRS, high-solid anaerobic digester with recycling seeds system; HSAD, high solid anaerobic digester; UASB, up-flow anaerobic sludge beds; OFMSW, organic fraction of municipal solid waste; TS, total solids; SRT, solids retention time; HRT, hydraulic retention time; VFA, volatile fatty acid.

Definitions

High solids waste: waste that includes from about 20 to about 30%, and usually from about 15 to about 25% solids, and most frequently from about 10 to about 20% (e.g. about 10, 15 or 20%) solids. Such waste may also be referred to herein as the "organic fraction of municipal solid waste" or "municipal waste".

High solids phase: a composition comprising from at least about 15 to about 50%, and usually from about 20 to about 45%, and more frequently from about 25 to about 40% (e.g. about 25, 30, 35, or 40%) solids during the first stage of digestion as described herein. Usually, the composition comprises at least about 35% solids.

Low solids phase: a composition comprising from about 0 to at most about 5%, and usually from about 0.1 to at most about 3%, and most frequently from about 0.5 to at most about 2% solids (e.g. about 0.5, 1, 1.5, 2.0, 2.5, 3, 3.5, 4.0 or 5% solids) during operation of the first stage of digestion as described herein. Usually, the composition comprises less than about 5% solids.

The "hydraulic retention time" (HRT), also known as "hydraulic residence time" or τ (tau), is a measure of the average length of time that a soluble compound remains in a constructed bioreactor. Hydraulic retention time is the volume of the aeration tank divided by the influent flow rate (volume of aeration tank/influent flow rate), where using SI Units Volume is in [$m^3$] and Influent flow rate is in [$m^3/h$]. HRT is usually expressed in hours (or sometimes days).

"Solids retention time" (SRT) refers to the length of time that solids are retained in a bioreactor and hence exposed to microbes that carry out digestion.

"Anaerobic microbial consortium" refers to a group of microbes (e.g. bacteria, fungi, etc.) that are used together to perform a desired task such as degrading substrates. Anaerobic microbial consortia may be comprised of different genera and species of microbes and generally, each species plays a different role in the desired task that complements the role of the other microbes, e.g. one type of microbe may break down large complex molecules that are subsequently further broken down by another type of microbe in the consortium, and the resulting products may be used by yet another type of microbe to generate a desired product. Anaerobic consortia or this type are described, for example, in United States patent application 20120021495 (Vanzin), the entire contents which is hereby incorporated by reference.

"Methanogen-rich anaerobic culture of microbes" refers to a culture of microbes, all of which are anaerobes (either facultative or obligate), which is enriched for those which are capable of producing methane. For example, such enriched cultures would usually contain at least about 50%-100% methanogens, and usually at least about 30, 35, 40, 45, 50, 55, 60, 65, 70, 75, 80, 85, 90 or 95% methanogens.

A major challenge for biogas production via microbial digestion of waste is the gradual reduction in pH caused by the accumulation of digestion products such a VFAs in the reaction milieu. While the prior art generally uses a single reactor for simplicity and pH phasing to address this problem, in the present technology the two concepts are blended by using two interconnected reactors, one of which contains, during operation, both a solid and a liquid phase. The use of such a system avoids the need for pH phasing. Instead, multiple factors are harnessed to control the pH and to achieve other advantages.

According to the present technology, soon after digestion is initiated in a single first reactor, separate solid and liquid phases are formed. Without being bound by theory it is believed that several factors contribute to the formation of the two phases, for example, the relatively low density of the waste solids and the flotation effect of the biogas produced in the low solids phase. Thus, the phases may be separated from each other via lifting of the solids by biogas generated during digestion. As a consequence, solids are retained or held in an upper solids layer (phase) in the reactor while liquid components of the reaction mixture tend to sink or settle to the bottom portion of the reactor, forming a low solids liquid phase. Significantly, organics and VFAs which are generated during digestion in the upper solids phase, and which over time would tend to cause an undesirable decrease in the pH (acidification) of the upper phase and inhibit digestion, are instead removed from the upper phase by passive diffusion into the lower liquid layer (phase). Efflux of the organics and VFAs by this mechanism attenuates or lessens the pH lowering effects they would otherwise exert, and the pH of the upper solids phase tends to be maintained within a range that is optimal or acceptable for digestion. Further pH control (and hence successful biogas generation) is promoted by the transfer of effluent from the lower liquid phase of the first reactor to a second reactor, which contains a low solids liquid medium suitable for generation of biogas. In addition, pH control (and hence augmentation of the digestion process) occurs when digested alkalinized effluent containing active bacterial mass is transferred from the second reactor back to first reactor. Using these mechanisms, and, optionally, a buffer tank as described below, the decrease in pH can be offset (negated, reversed, etc.), e.g. by at least from about 1-10 pH units, e.g. by about 1, 2, 3, 4, 5, 6, 7, 8, 9, or 10 pH units, and usually is offset by an amount that is sufficient to bring the pH back to and/or maintain the pH near neutrality, e.g. in the range of from about 6.0 to about 7.5. This multipronged mechanism of pH control results in enhanced kinetics and biogas (e.g. methane) production in both reactors, and thus a more stable system overall. Therefore, unlike traditional two-stage anaerobic digestion systems, the present systems advantageously produce methane in both digesters.

Accordingly, the present invention involves two-stage (acid and methane) and two-phase (solid and liquid) anaerobic digestion. The whole system includes two digesters: a first digester in which hydrolysis and acidogenesis are the predominant reactions, and a second reactor in which methanogenesis is the predominant reaction. Importantly, both digesters do involve methanogenesis, thus allowing for the controlled pH and production of methane in both reactors. The latter reactor may be referred to as the "high rate" reactor due to the rapid rate at which biogas is produced (synthesized) therein. Conditions within each reactor (e.g. temperature, pH, additives, composition (including microbe types, etc.) are selected or optimized to encourage either hydrolysis and acidogenesis (in the first reactor) or methanogenesis (in the second reactor). The system may also optionally include one or more buffer tanks connectedly interposed between the first and second reactors. Effluent from the first reactor may be passed through the buffer tank for processing (e.g. to increase the pH) prior to being transferred to the second reactor.

Two distinct phases reside in the first stage reactor, which is a high solid anaerobic digester (HSAD) capable of being operated in either batch or continuous mode, and capable of handling waste with high solids concentrations, e.g. in the range of from about 10 to about 30%. An exemplary initial feedstock may be about 30% TS, which may be diluted with mixing to from about 10-20%. During operation without mixing, an exemplary high solids phase primarily may comprise from about 20 to about 35% solids and a low solids liquid phase comprising from about 0 to about 3% solids may be formed, with the low solids liquid phase being located beneath (underneath, below) the high solids phase in the reactor. In other words, the high solids phase is positioned within a top portion of the reactor and the low solids liquid phase is positioned within a lower portion of the reactor. Significantly, this phase separation takes place without the input of energy. Rather, digestion takes place in both phases, producing biogases, which migrate upward and permeate the upper solids phase, causing the solids to "float" within the reactor, e.g. the solids are buoyed up by the biogases. (The solids may also float due to their relative density or buoyancy, compared to the liquid phase). Further, as described above, various compounds that are produced during digestion in the solid phase continually diffuse into the liquid phase where they may be digested to create more biogas and/or removed when liquid from the liquid phase is removed from the first reactor.

This differential positioning (i.e. the locations of) the two phases is/are generally caused by and maintained (e.g. continually regenerated) throughout (during) the entire digestion procedure, e.g. during the procedure that is carried out during one batch or "cycle" of use of the reactor, or indefinitely if a continuous procedure is employed. In some embodiments, the lower liquid phase is generated only as the outcome of digestion due to biogas floatation and low specific gravity of solid waste. In exemplary embodiments, in a first HSAD reactor, the first stage naturally separates into two zones due to biogas floatation and the low specific gravity of solid waste compared to water.

Therefore, one feature of the present technology is the use of the liquid-solid separation that occurs naturally during operation of the first digester. The liquid-solid separation is advantageous in order to stabilize the system. For example, non-rapid removal of VFAs produced during organic degradation generally results in pH depression, which slows degradation kinetics in the high solids phase, and poses a potential risk death of the microbes in the reactor, unless the VFAs are removed from the site of reaction. Thus, by introducing a natural separation mechanism that allows the VFAs to follow the concentration gradient and passively diffuse into the bottom liquid layer, from whence they can be completely removed (e.g. by drained the liquid phase from the reactor or pumping it into a second reactor as discussed above), rapid separation and hence pH control is maintained. Experimental results presented herein show that such a separation readily occurs in the first reactor due to the relatively low density of food waste and the flotation properties imparted by biogas. Therefore, additional equipment is not needed to separate digesting solids from liquids, and the efficiency of the whole treatment system is increased and costs are reduced.

Another feature of the present technology is provision of effective mixing mechanisms in the first digester. In general, mixing may be used to reduce energy consumption and enhance access of the microbes to substrate, which in turn aids in substrate digestion and diffusion of products into the liquid phase. Firstly, biogas produced within the media floats upward and pushes solids up to the top of the reactor while allowing for settling of liquids and diffusion soluble organics (e.g. VFAs) into the bottom layer, affording one means of mixing. In addition, in some embodiments the effluent from the second reactor may be introduced into the high solids digester e.g. at the top inlet to produce additional mixing. This also results in dilution of the high solids phase (e.g. to compensate for effluent removed from the liquid phase), and to break up scum, which may form on the surface of the high solids phase. Second reactor effluent may be introduced into the first reactor (usually at the top), e.g. by spraying, by introduction of one or more (e.g. multiple, or a plurality of) liquid streams, which may be under pressure, or by any other suitable means. In addition, other suitable mixing mechanisms known in the art may be employed. For example, in some embodiments, mechanical mixing may be used as needed to break up the solid waste in the top layer, and/or to remove any "scum" that might be produced during digestion, a common problem in many anaerobic digesters. Among these three mixing modes, only mechanical mixing requires consumption or input of additional energy. For the mechanical mixing, in one embodiment, radial flow impellers are used to impose shear stress and break up solid clumps in the high solids phase. This type of impeller is relatively inexpensive and the food waste to be stirred is generally soft enough to be agitated in this manner. In some embodiments, further cost-savings may be accrued by using intermittent mechanical mixing only as needed, e.g. by cycling mixing on and off or by delivering bursts of mixing, to supplement the mixing contributions of biogas and second reactor liquid effluent.

In some embodiments, during operation of the reactors, a portion of the liquid phase from the bottom of the first stage digester is removed from the first reactor and transferred to a second reactor such as a high-rate digester. This second reactor provides a site or location for further anaerobic treatment (digestion) of soluble organics in the liquid stream to produce biogas (especially methane). In addition, the second reactor may be used to produce high alkalinity liquid effluent, which, in some embodiments, is sent or transferred back to the first stage reactor. Introduction of this effluent into the first reactor provides multiple advantages, such as further control of the pH (reduction of acidity due to enhanced alkalinity of effluent); mixing/dilution of the high solids to manipulate phase density and/or consistency as described above, e.g. in order to optimize reaction kinetics; etc. In some embodiments, effluent from the second reactor provides a means to modulate/control the constituent components of the high solids phase. For example, the second reactor may serve as a seed reactor to generate bacterial and archae seed to add to the first reactor, as described in detail below.

Exemplary types of second reactors include but are not limited to up-flow anaerobic sludge bed (UASB) reactors, anaerobic sequencing batch reactors (ASBRs), anaerobic biofilm reactors (ABRs), etc. Because the feedstock for second reactors such as UASB seed reactors is required to be less than 1% TS, in prior art systems, a separate step of separating solids is required prior to such a transfer. The present system advantageously does not require an extra step of separation due to the phase separation that occurs in the first reactor, i.e. a suitable low level of solids is present in the lower liquid phase.

In some embodiments, the present technology provides a mechanism whereby seeds of the methanogenic bacteria as well as the other anaerobic microbial consortia utilized in the second reactor are advantageously recycled into the first reactor. For an exemplary UASB reactor, the sludge blanket is comprised of microbial granules, i.e. small agglomerations (about 0.5 to about 2 mm in diameter) of microorganisms that, because of their weight, resist being washed out in the up flow. However, the microorganisms attached to the external surface of the granules can be carried out by the effluent of the UASB seed reactor, with the carrying capacity depending on the up flow velocity and outflow position(s) in the seed reactor. Introduction of these organisms into the first reactor via the second reactor effluent provides an ongoing fresh supply of actively metabolizing methanogens to carry out digestion of the solid waste in the first reactor. Generally, the concentration of seed methanogens that is transferred from the second reactor to the first reactor is from about 0 to about 5% of the TS, e.g. about 0.1, 0.5, 1.0, 1.5, 2.0, 2.5, 3.0, 3.5, 4.0, 4.5, or 5%.

In order to optimize or encourage hydrolysis and acidogenesis in reactor #1 and methanogenesis in reactor #2, the pH of the first reactor is generally maintained in a range of from about 6.0 to 7.5 (e.g. 6.0, 6.1, 6.2, 6.3, 6.4, 6.5, 6.6, 6.7, 6.8, 6.9, 7.0, 7.1, 7.2, 7.3, 7.4, or 7.5) while the pH of the second reactor is maintained in a range of from about 6.5 to 8.5 (e.g. 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, or 8.5). Notably, while traditional two-phase literature identifies a stratified pH approach as beneficial to organics degradation, data presented herein shows that control of pH above 6.0 and near neutral in both reactors can enhance organic degradation kinetics while allowing for production of methane in both reactors.

Recycling the liquid between the first reactor and the second reactor also provides a convenient path for nutrient removal and recovery from the digester, increasing the overall economic value of the system. This is because the liquid stream from the first reactor contains the majority of nitrogen and phosphorus produced by the anaerobic degradation process, which breaks down insoluble organic nutrients into soluble inorganic forms. Therefore, in some embodiments a bypass or means of egress for a portion of the effluent from the first reactor is introduced, whereby a portion of the first reactor effluent goes to a nutrient recovery treatment while the remainder follows its path of transfer to the second reactor. Alternatively, in some embodiments, a bypass or means of egress for a portion of the effluent from the second reactor (which contains the nutrients because they were transferred from the first reactor where they were produced) is introduced, whereby a portion of the second reactor effluent goes to a nutrient recovery treatment while the remainder follows its path of recycling to the first reactor. Accordingly, optional means for removing effluent from the first reactor, the second reactor and/or, if present, the buffer tank may also be present in the system. The most preferable route for nutrient removal is from the second reactor. In some embodiments, nutrients are removed from effluent before the effluent is reintroduced into the first reactor, or, when a bypass buffer tank is present, from the buffer tank. Means for removing nutrient rich-effluent typically include, for example, various valves, pipes, conduits, etc. through which the effluent can egress. In this manner, nutrients can be efficiently 'scrubbed' or removed continuously from the system. As a result, there is little or no inhibition due to accumulation of nutrients, such as ammonia, allowing for better process control of the entire digestion reaction and greater environmental sustainability, since it is possible to divert the nutrients e.g. to the production of bio-fertilizers. Other prior art systems, with designs that are not efficiently able to separate out and divert liquid streams, are not amenable to such fractionation. Those of skill in the art are familiar with means to recover nutrients. For example, see U.S. Pat. Nos. 6,524,632 (Kartchner) and 6,682,578 and 6,846,343, both to Sower.

In some embodiments of the technology provided herein, biogas from the first reactor (e.g. primarily methane, carbon dioxide and hydrogen) is fed into the second reactor. The feedstock of municipal wastes generally contains higher percentages of VFAs and easily degradable substrates than do other types of waste. Thus, when this type of solid waste initially contacts microorganisms in the high solids phase in the first digester, a high volume of $CO_2$, and $H_2$ are produced and released very rapidly. Release may be so rapid that the methanogens present in the first digester cannot capture and covert these gases into methane, even at a pH greater than 6.0. Thus, in order to recapture this methane production potential, in some embodiments the biogas that is produced in the first reactor, especially initially, is introduced into the second reactor. This transfer allows a practitioner of the method to implement longer retention times in the system overall.

In some embodiments, the first reactor is operated in batch mode, and Solid Retention Time (SRT), is maintained from about 7 days to about 12 days. Alternatively, if the first reactor is operated in continuous mode, SRT may be maintained e.g. for more than 30 days. In some embodiments, the link between the first reactor and the second reactor may eventually be closed or shut down, since excessive introduction of $CO_2$ from the first reactor to the second reactor can reduce the pH of the low solids liquid medium, thereby acidifying the effluent of the second reactor and decreasing or eliminating the ability to modulate pH control of the first reactor by transferring effluent from the second reactor.

In some embodiments, e.g. when a UASB seed reactor is utilized as the second reactor, intense hydrolysis of solid wastes (i.e. the hydraulic retention time (HRT)) is allowed to proceed in the second reactor for a period of time ranging from about 6 hours to about 48 hours, or from about 12 hours to about 36 hours, and usually from about at least about 24 hours to at most about 48 hours. However, shorter and longer HRTs are also contemplated. In some embodiments, HRT is about 1 day.

Figure 16:
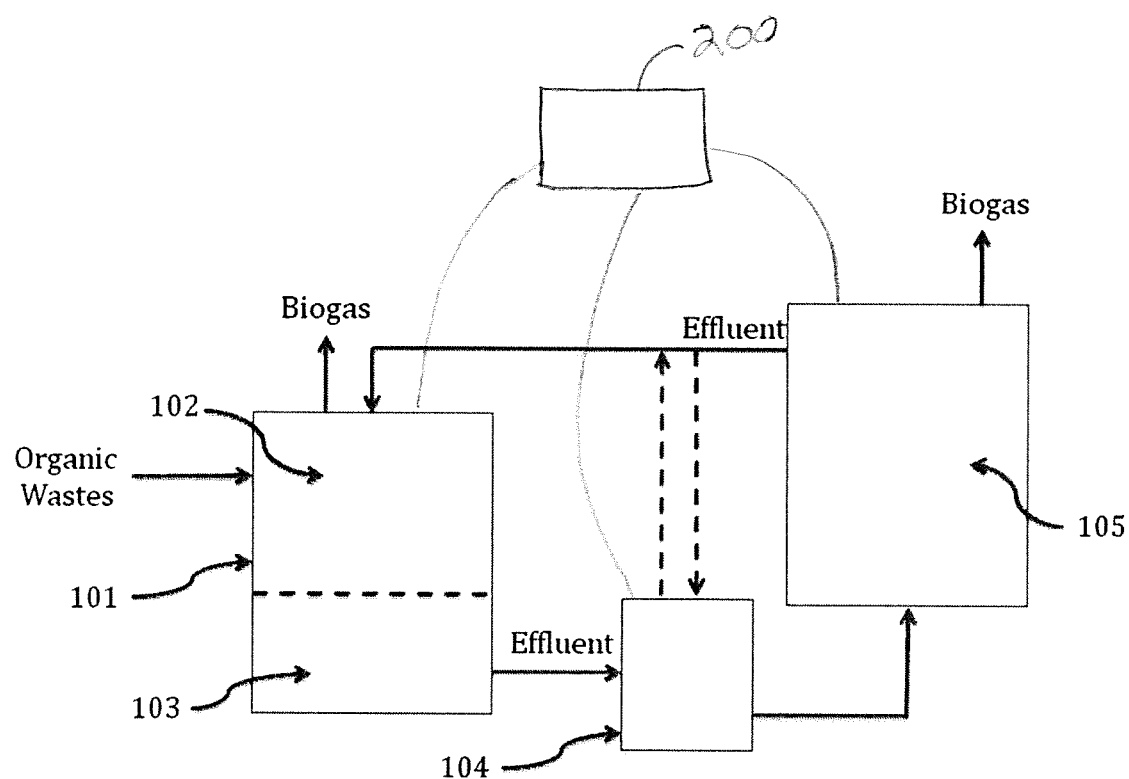
FIG. 16 is a schematic representation of a two-stage anaerobic digester system

A schematic of the two-stage anaerobic digester system as described herein is provided in FIG. 16. As can be seen, a first, high solids stage of digestion is housed within a single reactor 101. During operation, reactor 101 contains high solids phase 102, and low solids phase 103, with total solids within reactor 101 being in the range of from about 5% to about 30%, or from about 10% to about 20%. High solids phase 102 provides conditions for hydrolysis of high solids organic wastes, and low solids phase 103 comprises a liquid methanogenic phase capable of generating biogas such as methane. The two phases are in direct diffusive communication with each other, e.g. high solids phase 102 "floats" or is suspended directly on low solids phase 103. In some embodiments, high solids phase 102 and low solids phase 103 are optionally separated from each other by a grate, screen, sieve or similar permeable (or semi-permeable or selectively permeable) physical barrier that does not inhibit or impede the free exchange of aqueous gases, salts, particulates and organics between high solids phase 102 and low solids phase 103, but which does impede other components of the high solids phase 102 from sinking into low solids phase 103. Effluent from low solids phase 103 may be fed directly into a second, low solids liquid medium contained within reactor 105. Alternatively, effluent from 103 may be fed into optional buffer tank 104. In buffer tank 104, effluent from low solids phase 103 may be treated with effluent from reactor 105 or with other chemical compounds or physical means to modify the effluent's pH, nutrient content, solid content, microbial population and/or other physical characteristics of the effluent, prior to its introduction into reactor 105. In one embodiment, reactor 105 comprises an up-flow anaerobic sludge bed reactor.

In one embodiment, dispersion of solids in high solids phase 102 is accomplished by the generally upward, bubbling movement up and through the medium and into the solid phase of gases generated in low solids phase 103. In one aspect, low solids phase 103 thus provides a mixing mechanism during digestion within solid phase 102. In addition, a mechanical mixing means (e.g. using propellers, blades, a stirring or agitating apparatus, etc.) and/or a liquid-liquid mixing means (e.g. by spraying or injecting a stream or streams of the effluent from 105 into 102, e.g. at or near the top) may also be employed. If mechanical mixing is employed, in particular embodiments radial flow impellers may be used to impose shear stress to the fluid and break up the solid clumps of the waste materials in the high solids phase, 102.

In some embodiments, the effluent from 105 may optionally be cycled through buffer tank 104 prior to introduction into 102, e.g. for chemical or physical modification as described above. In some embodiments, a fraction of the effluent from 105 is fed to buffer tank 104 and a fraction is fed to high solids phase 102.

The specific ratio of the volume of reactor 101 to the volume of reactor 105 can also serve to balance the system. For example, adjusting or balancing the volumes of reactor 101 and reactor 105 can be used to correct for disparate rates of hydrolysis and acidogenesis processes in reactor 101 relative to the rate of methanogenesis in reactor 105. Specifically, the rates of hydrolysis and acidogenesis are generally faster than methanogenesis, and thus the relative volume of reactor 105 in which methanogenisis processes are dominant should be larger that that of reactor 101. A skilled artisan will recognize that the specific ratio will depend on the nature of the organic wastes, the microbes that are utilized, and the precise operating conditions selected for the digester system. In some embodiments, the volume of reactor 105 is from about 1 to about 4 times the volume of reactor 101.

In some embodiments, reactor 101 may be or may comprise a high solid anaerobic digester (HSAD) and reactor 105 may be or comprise an up-flow anaerobic sludge bed (UASB) seed reactor. In a particular embodiment wherein reactor 105 comprises a UASB seed reactor, a means to recycle the seeds of the anaerobic microbial consortia from reactor 105 to reactor 101 may be provided. The sludge blanket within such a UASB seed reactor is preferably comprised of microbial granules, i.e. small agglomerations (e.g. from about 0.5 to about 2 mm in diameter) of microorganisms that, because of their weight, resist being washed out in the upflow. However, the microorganisms attached on the external surface of the microbial granules can be separated from the granules (e.g. through shearing by upflow of liquid) and carried out in the effluent of the UASB seed reactor and into reactor 101. The carrying capacity (concentration of microbes in the effluent) depends on the upflow velocity and the positioning of the outflow mechanism in the UASB seed reactor, and is generally in the range of from about 0 to about 5% of TS (e.g. about 0.5, 1, 1.5, 2.0, 2.5, 3.0, 3.5, 4.0, 4.5 or 5.0%).

Municipal Solid Wastes (MSW), commonly known as trash or garbage, is a waste type comprising principally everyday consumable and/or disposable items. MSW is comprised predominantly of food wastes, yard wastes, containers and product packaging, and other miscellaneous inorganic wastes from residential, commercial, institutional, and industrial sources. In one embodiment, the organic waste that is processed by the system described herein consists, at least in part, of food waste and other organic materials, woody debris, paper packaging and paper products. Organic wastes having a solids concentration of at least about 30 percent may be introduced continuously or intermittently at or near the top of reactor 101. The organic wastes may be optionally chopped, shredded, pulverized or ground prior to introduction into reactor 101. Food waste in particular significantly increases the production of volatile fatty acids (VFAs), and consequently an increase in the methane productivity, in the systems described herein. In some embodiments, the total solids (TS) present in high solids phase 102 are maintained at a level of from about 5% to about 30% or from about 10 to about 20%. In contrast, the TS of reactor 105 are generally maintained at a level of less than about 5%, e.g. about 3%.

A pre-sorting system may or may not be utilized to separate organic waste from the MSW prior to introduction into the anaerobic digester system described herein. In particular embodiments, removal of high-density contaminants such as glass and metal can be achieved either beforehand, or during or after digestion within reactor 101 since they sink to the bottom of the reactor, from whence they may be directly discharged from the reactor 101.

Any active psychrophilic, mesophilic and thermophilic microbial anaerobic digestion system can be employed in the practice of the present invention. The preferred microbial seeds recycled from the UASB seed reactor include Methanobacteriaceae, Methanosarcinaceae, Methanosaetaceae, Methanocorpusculaceae, Methanomicrobiaceae, and other archae organisms. The species from genera include, but not limited to, *Methanobacterium formicicum, Mb. thermoautotrophicum, Mb. bryantii, Mb. wolfei, M.b uliginosum, M.b alcaliphilum, Methanobrevibacter ruminantium, Mb. smithii, Mb. arboriphilicus, Methanothermus fervidus, Methanococcus vannielii, Mc. voltae, Mc. thermolithotrophicus, Mc. maripaludis, Mc. jannaschii, Mc. halophilus, Methanospirillum hungatei, Methanomicrobium mobile, Mm. paynteri, Methanogenium caraci, Mg. marisnigri, Mg. thermophilicum, Mg. aggregans, Mg. bourgense, Methanosarcina barkeri, Ms. Mazei, Ms. Acetivorans, Ms. Thermophila, Methanoplanus limicola, Methanococcoides methylutens, Methanolobus tindarius, Methanothrix soehngnii, Mt. concilii, Methanosphaera stadmanae* etc.

The two phases present in reactor 101 operate in a synergistic manner that is the result of the distinct physical and chemical conditions in solid phase 102 and solid phase 103, respectively. The biodegradable solids and oxygen tolerant microorganisms naturally concentrate toward the top of reactor 101 in high solids phase 102. This is likely due to the high concentration of organic wastes in high solids phase 102 and physical agitation of the phase, which results in a higher relative oxygen concentration there compared to the lower low solids phase. These conditions favor the bacterial populations that both hydrolyze and produce VFAs from the organic wastes. The soluble hydrolysis products and VFAs are unaffected by the floatation effects and freely diffuse throughout the reactor 101, e.g. into low solids phase 103.

Low solids phase 103 is largely stagnant. Without agitation, low solids phase 103 contains a relatively low concentration of oxygen and therefore provides conditions favorable for microbial populations that perform anaerobic processes that produce biogases. In low solids phase 103, methanogenic bacterial populations utilize the VFAs and hydrolysis products produced in high solids phase 102 to generate methane and other biogases that help to suspend the solid phase, and which can also be collected, e.g. to produce energy, to be utilized for chemical processes, etc. As discussed above, the effluent from low solids phase 103 can be fed directly into reactor 105 or optionally into buffer tank 104 to undergo treatment. Accordingly, suitable environmental conditions for reactors 101 and 105, such as VFA concentrations, pH, temperature, nutrients and retention time, can be accommodated or facilitated by optional buffer tank 104. Treatments may comprise chemical or physical modification of the effluent's pH, nutrient content, solid content, microbial populations and/or other physical characteristics of the effluent. Treated effluent may be either reintroduced into reactor 101 or transferred to reactor 105. In particular embodiments, buffer tank 104 may also be used as a means to implement a solids removal step whereby undigested solids from reactor 101 are removed from the liquid fraction and, for example, added back to reactor 101.
Exemplary Two Phase Two Stage Anaerobic Digester Systems A wide range of temperature conditions are acceptable in a system using, for example, an HADRS system for reactor 101 and a USAB reactor for reactor 105. Suitable operating conditions for both reactors range from about 13 to about 70° C., and are usually between from about 30 to about 40° C. Typically, in such systems, methanogenesis is regarded as the rate-limiting step. Thus, in some embodiments, reactor 105 is a high rate USAB methanogenic (methane-producing) digester. Such a reactor allows low temperature operation and high upflow rates. For example, in UASB digesters at mesophilic temperatures of 30-38° C., removal of organics above 70% (as measured by chemical oxygen demand (COD)) have been reported by several authors. At lower ambient temperatures, overall performance deteriorated with COD removals of 65% at 20° C. and 55-65% at 13-17° C. At low temperatures, the performance of intensive anaerobic systems is highly limited by competing hydrolysis of suspended solids and/or decreases in organic matter degradation, which accumulates in the sludge bed. It has been observed that the relatively high concentration of particulate matter in domestic wastewater (around 350 mg/l total suspended solids (TSS)) has lower degradation rates at psychrophilic temperatures. However, for those studies, which were carried out at a much lower temperature (4° C.), the food waste was acidified, which may have contributed to the observed result. Installation and use of a mechanical mixer in HADRS systems can accelerate hydrolysis and acidification in the first reactor. Thus, an HADRS system has excellent potential for use at psychrophilic temperatures.

Furthermore, the granules whose surface area is covered with aggregations of bacteria advantageously have good settling properties and are not susceptible to washout from HADRS systems under practical reactor conditions. Retention of active sludge, either granular or flocculent, within a UASB seed reactor enables good treatment performance at high organic loading rates. The UASB seed reactor can be used at organic loading rates of up to 40 kg $COD/m^3/d$ and at high upflow velocities in the range of 4 to 10 mph. This wide range of flow rates effectively accommodates seeding of anaerobic microorganisms, pH control and mixing in the first reactor to remove inhibitory factors and stabilize whole system.

FIG. 1. shows a schematic representation of an exemplary HADRS system and can be used to describe the basic operation of one embodiment of a two-stage and two-phase high solid anaerobic digestion system. In this embodiment, the digester 1 is an HSAD reactor and digester 2 is a UASB seed reactor. One-stage and two-phase anaerobic digestion occurs in digester 1. The two phases are an upper agitation zone and a lower stagnant zone. The upper agitation zone is mainly dominated by hydrolytic and acidogenic bacteria which prefer intensive mixing, whereas the lower stagnant zone is mainly dominated by methanogenic bacteria, which prefer mild mixing conditions. Digester 1 mainly produces VFAs while digester 2 mainly produces methane.

To implement the methods of the invention, OFMSW, which is mainly food waste and other organic material, woody debris, paper packaging and paper products, is coarsely shredded and placed into the top of digester 1. In some embodiments, feedstock comprising about 30 to about 100 percent solids is continuously or intermittently introduced into digester 1 to provide a relatively constant volume for the high solids phase for digestion. In this embodiment, effluent recycled from digester 2 is continuously or intermittently sprayed into the top of digester 1 to dilute the feedstock, for seeding the upper high solids phase with active microorganisms, for pH control, and for mixing. The amount of active microorganisms, especially methane-forming bacteria, is adjusted by the upflow rate and outflow position(s) of digester 2. In digester 1, the total solids (TS) are maintained from about 10% to about 35% in the upper high solids phase. Liquid and solid phases are naturally separated in digester 1 in less than one day due to the relatively light density of food waste and the flotation effects of biogas. The organic fraction of solid wastes is suspended in the upper portion and aggregates into large clumps while liquid is accumulated in the middle and lower portion of digester 1. VFAs produced in the upper high solids phase migrate into the lower liquid phase. Heavy contaminants such as glass and metal settle down into the bottom of digester 1 and may be directly discharged out of the digester. In the upper agitation zone, intermittent or continuous mechanical mixing is used to break up the large clumps of solid waste that forms, thereby increasing contact between microorganisms and solid substrates, enhance mass transfer, and accelerate the digestion process. High-shear impellers (such as Bar Turbine propellers) are generally employed, but other types of mixers may also be used to break up the solid clumps. In the lower stagnant zone, the (generally upward) movement of biogas (e.g. bubbling) produced by microorganisms in the liquid also provides mild mixing for both phases. In addition, as described above, other modes of mixing may be employed, e.g. mechanical mixing, mixing via a spray or stream of effluent from the seed reactor, etc. Among these modes, only mechanical mixing requires the input of additional energy. Therefore, a low cost but effective mixing strategy can be developed by using various combinations of mixing modes.

In the lower portion of digester 1, liquid comprising VFAs and particles of e.g. undigested organic matter may be continuously or intermittently discharged (e.g. from a side conduit) into the top of buffer tank 3 for various treatments as described above. Gravity discharge is preferred for cost saving but a pumping mechanism may also be employed. In some embodiments, residual, non-biodegradable components are intermittently withdrawn from the bottom conduit, e.g. for use as compost and/or simply for disposal, to aid in providing suitable SRT conditions within digester 1.

As described above, buffer tank 3 provides communication and facilitates balance between digester 1 and digester 2. Suitable environmental conditions for digester 1 and digester 2 such as VFA, pH, temperature, nutrients and retention time can be accommodated or implemented by the use of buffer tank 3. In some embodiments, liquid is continuously pumped to the bottom of digester 2 e.g. from a side conduit located at the lower portion of buffer tank 3, while residuals and non-biodegradable components are intermittently withdrawn from the bottom conduit of buffer tank 3.

Most of methane is produced by the system is generated in digester 2. Digester effluent is continuously discharged from multiple positions, usually at or near the top of digester 2, and into the top of digester 1 and/or to buffer tank 3. Again, gravity discharge is preferred due to cost saving; however, pumping means may also be employed. As discussed above, the effluent from digester 2 plays different roles when recycled into digester 1 and buffer tank 3. When recycled into digester 1, the effluent can provide seeding of anaerobic microorganisms, pH control, and mixing. When recycled into buffer tank 3, the effluent can be treated so as to ultimately serve to increase HRT in digester 2.

In some embodiments, the biogas initially produced in digester 1 is sent to digester 2 for longer retention (e.g. about 1 to 2 days) in order to produce more methane. As noted above, this is because the feedstock of food waste contains a higher percentage of VFA and easily degradable substrates so that when the solid waste initially contacts microorganisms in the reactor, high volumes of $CO_2$ and $H_2$ are produced and released so rapidly that methanogenic bacteria cannot capture and convert them into methane, even at a pH greater than 6.5. Transfer of these gases to digester/reactor 2 permits their conversion to methane.

In some embodiments, the system also includes a controller (controller 200 in FIG. 16), which may comprise or be software (e.g. a computer program) executable by a computer or a computerized device, either on site or at a distance. The controller can execute a program designed to cause the system described herein to carry out the methods described herein. Alternatively, or in addition, the controller is capable of using data obtained by sensors e.g. pH, temperature, flow rate, optical density, mixing rate, time, and other types of sensors suitable for monitoring conditions within the reactors and buffer tanks, and/or within lines or connections between them. The controller can adjust or cause adjustments in the operation of the system to achieve optimal or desired results with respect to biogas production, or for any other purpose. For example, the controller can increase or decrease flow rates of effluent from the first reactor to the second reactor and vice versa, in response to changes in pH that are detected, and monitor and adjust temperatures (e.g. by activating heating or cooling means), and can also adjust other parameters described herein. In addition to receiving and processing input from sensors, the controller can receive and process input from humans, e.g. additional input such as desired time of operation or other desired end points, information about culture compositions, etc.

In Washington State, where more than 900,000 tons of waste per year enters landfill approximately 18 percent of that waste is food waste. And, as indicated by the 2009 Washington Statewide Waste Characterization Study, food waste and other organic materials, woody debris, paper packaging and paper products make up more than 55 percent of the total waste stream. At more than 2.7 million tons, organic material swamps the landfills. In addition to new organics collection programs, many programs now collect more diverse materials, such as food waste, soiled paper and some compostable plastics in an effort to reduce landfill waste. However, food waste may cause problems at composting facilities since it rots very quickly, releasing noxious odors. Food waste is also associated with high contamination by plastic, metal, and glass, which is a disadvantage for composting. Use of the technology described herein can significantly abate the problems associated with food waste disposal by converting it to biogas.

Unlike two-stage anaerobic digestion described in the prior art, the high-solid anaerobic digester system described herein preferentially produces methane in both stages. In other words, methane is produced in and can be recovered from both the first reactor and the second reactor. Those of skill in the art are familiar with means to recover biogases such as methane. For example, see U.S. Pat. No. 6,524,632 (Kartchner) and U.S. Pat. Nos. 6,682,578 and 6,846,343, both to Sower.

EXAMPLES

Food waste was selected as the feedstock in the experiments described herein due to its high potential for energy and fertilizer production. Food waste was collected from the Washington State University (WSU) cafeteria where it had been shredded into small sizes ranging from 0.5 to 3 cm. The density of the different total food materials is 1.002-1.012 g/m³, and the dry density of food waste is 1.04-1.11 g/m³, i.e. very close to that of water, so the food waste can be easily suspended in water. The total solids (TS) in the reactions described herein were about 30%. Anaerobic granular methanogen inoculants were obtained from Tri-Cities, Washington State. The HADRS system that was utilized was used in a heated room where the temperature was maintained at 35° C. (Aquaculture Lab at WSU). Anaerobic granular inocula were poured into each of two UASB seed reactors, so that each gallon of reactor volume contained about 2 kg of chemical oxygen demand (COD)/m³) of methanogens. Food waste often has low pH (less than 5.5) even after storage at low temperature and the pH was thus adjusted to 6.0-7.0 by effluent from the UASB reactor.

The UASB seed reactor was started up first by _the food waste with less than 5% TS. The initial pH in the UASB reactor was 7.5. For start-up, the 30% TS cafeteria food waste was diluted to less than 5% TS in the high solids digester using the effluent from an operational UASB seed reactor. Thereafter, gradually over a period of 2-3 days, the TS fed into the high solids digester was increased to 10-20%. The recycle rate of effluent from the seed reactor to the high solids digester was maintained at 51 gal/day.

1. Optimization of Hydrolysis and Acidogenesis Processes

Figure 2:
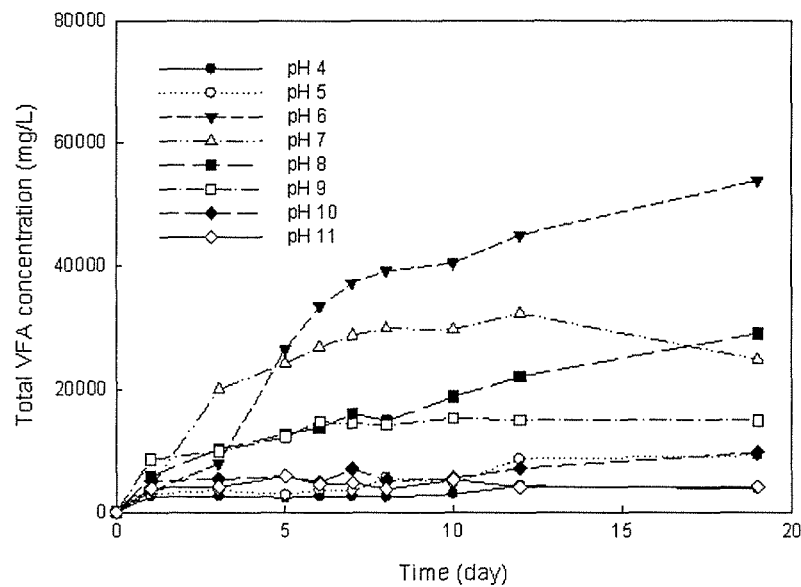
FIG. 2 is change of total volatile fatty acids (VFAs) with time at the different pH

FIG. 2 shows the change of total VFA produced over time at different pH values. As can be seen, the total VFAs rise steeply during the first several days, then increases slowly. A significant change in total VFA occurred at pH values between 6 and 7, and the highest VFA productivity is obtained in this pH range. The conclusion is that the optimum pH for anaerobic digestion is normally in the range of 6.0-8.0, and pH levels that deviate significantly from this range can indicate potential toxicity and failure of the digestion reaction. At pH levels below 6.0, acidic conditions can become toxic to methanogenic bacteria.

Figure 3:
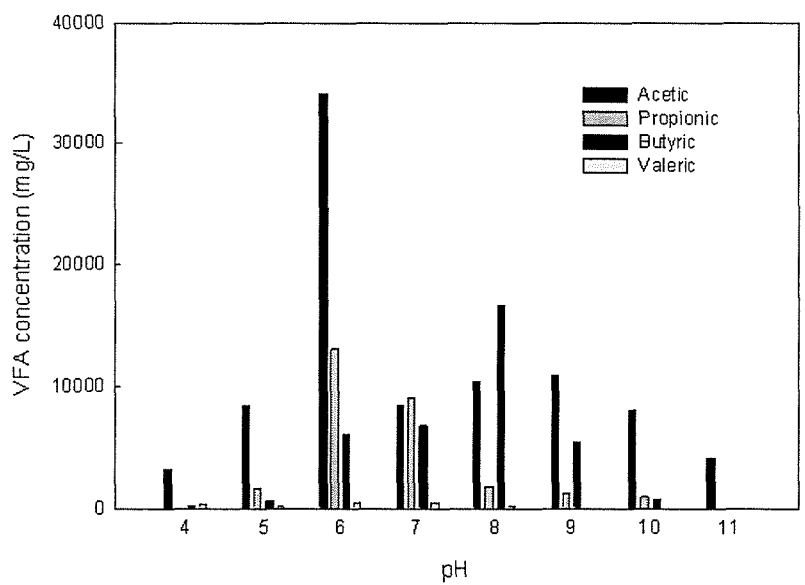
FIG. 3 is change of VFA concentrations with pH

FIG. 3 shows that the VFA profile of the digestion composition varies with pH, and FIG. 4 shows that TS reduction also varies with pH. All these results show that the optimum pH range for hydrolysis and acidogenesis in the high solids digester is from 6.0-8.0. Therefore, the pH in the high solids digester should be greater than 6.0 to achieve optimal production of bio-methane and high VFA production. Thus, enough effluent should be recycled from the UASB seed reactors to maintain an appropriate pH in the high solids digester.

2. Liquid-Solid Separation

VFAs produced in the high solids digester must be removed from the reactor quickly. Otherwise, they accumulate and cause a decrease in pH and overall failure of the operation. Traditional European high solids digestion technologies depend on recycling aliquots of the treated solids to maintain enough bacteria in the digester to consume the VFA that is produced. However, additional reactor volume and expensive equipment are required to do so. In some embodiments, the present technology provides improved technology for separating liquid and solid phases based on the experimental observations described below, making it possible to simply remove portions of the liquid phase from the reactor in order to maintain a suitable pH, which is much easier than removing solids.

FIGS. 5A and B show the natural separation of liquid and solid phases that occurs during hydrolysis and acidogenesis of high solids waste. In both A and B, the left bottle was filled with a mixture of food waste and methanogenic inocula from the effluent of a UASB seed reactor and the right bottle was filled with food waste and water. As can be seen in FIG. 5A, more biogas was produced in the left bottle and the biogas pushed the food waste up to the top in less than one day. The highest TS of food waste aggregated in the top level was 22%. In the right bottle, the food waste floated up slowly and separation of liquid and solid phases cannot be observed until the second day (FIG. 5B). This indicates that this phenomenon can be used as a separation technique for solids digesters, without the need for additional power input.

3. Experiments of the HSAD Reactor

Figure 6:
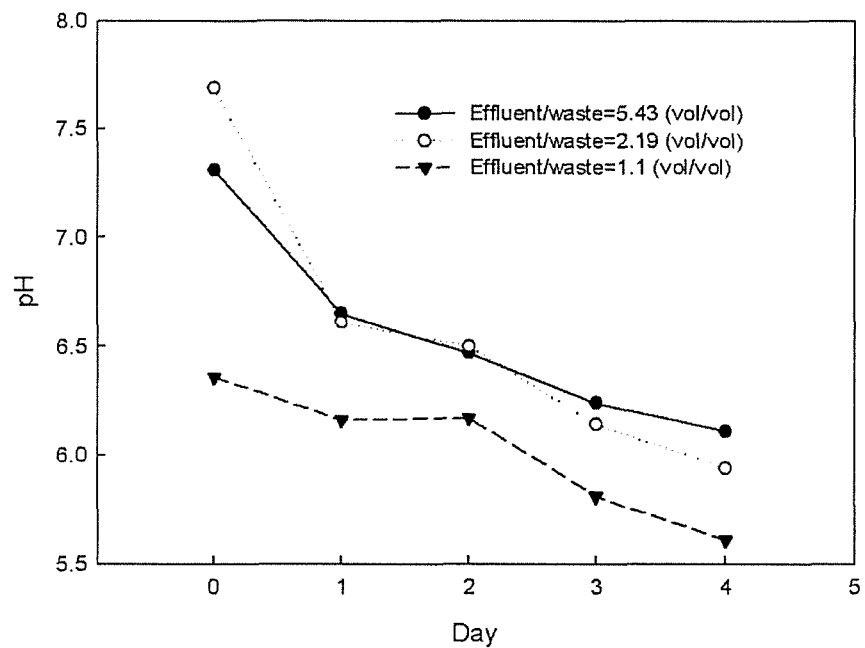
FIG. 6 shows the effect of recirculation ratio on the pH of the high solid anaerobic digester (HSAD) reactor.

FIG. 6 shows the effect of ratios of re-circulated effluent to water on the pH of the high solids digester. At the beginning, the pH of the food waste fed into the high solids digester was 4.5-5.5 while the pH of the effluent was 7.9. As can be seen, the pH in the high solids digester decreased with time in each case, and also decreased with a decrease in the rate of effluent recirculation. These results suggest that HRTs of less than 1 day can maintain a pH over 6.0 even at low recirculation ratios. Low recirculation ratios mean that UASB seed reactors with lower volumes can be used in the systems described herein, thereby reducing costs.

Figure 7:
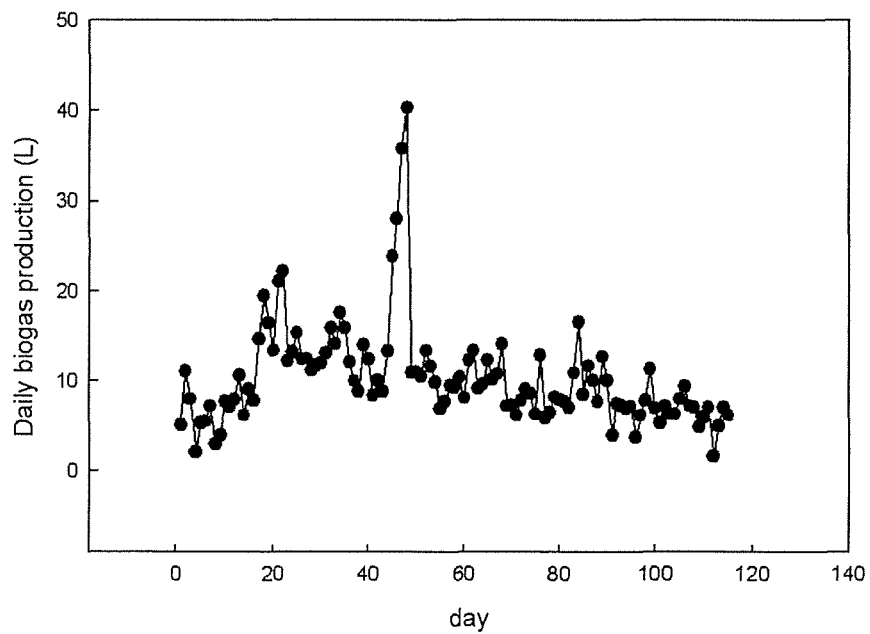
FIG. 7 shows daily biogas productions in the HSAD reactor

FIG. 7 shows daily biogas production in the high solids digester. As can be seen, the average biogas production was about 10 L/day, with the highest production being 40 L/day. The pH of the high solids digester was maintained between 6.5-7.5 throughout, and the high solids digester showed stable operation on a daily and monthly basis. No trend towards acidification occurred while effluent was recycled into the high solids digester from the second reactor. As predicted, on the first day, more effluent was required to remove the VFA and maintain pH in the high solids digester, since long-term storage of food waste results in degradation and hence the initial production of more VFA, even at low temperatures.

4. Experiments with the UASB Seed Reactor

Figure 8:
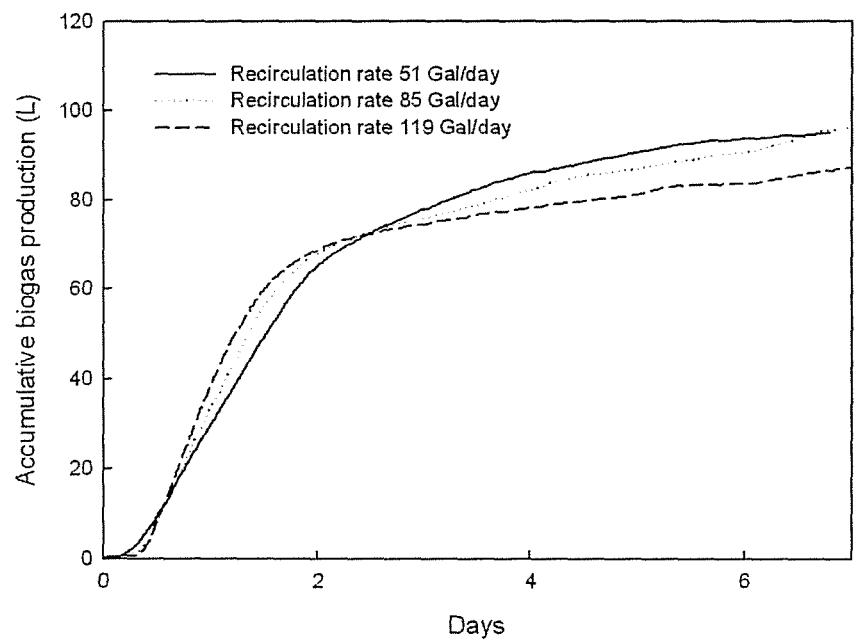
FIG. 8 is cumulative biogas production at a feeding rate of 10 gal/week in the UASB seed reactor.

FIG. 8 shows the cumulative biogas production (i.e. the total amount of all biogas produced) in the UASB seed reactor when the feed rate of leachate from the high solids digester is set at 10 gal/week. For this experiment, recirculation of effluent was carried out between the UASB seed reactor and a buffer tank at the indicated recirculation rates. As can be seen, the results showed that biogas production began at a high rate and then slowed over time. Further, a higher recirculation rate enhanced biogas production rate up until day 2, suggesting that the HRT in the UASB seed reactor can be less than 1 day.

Figure 9:
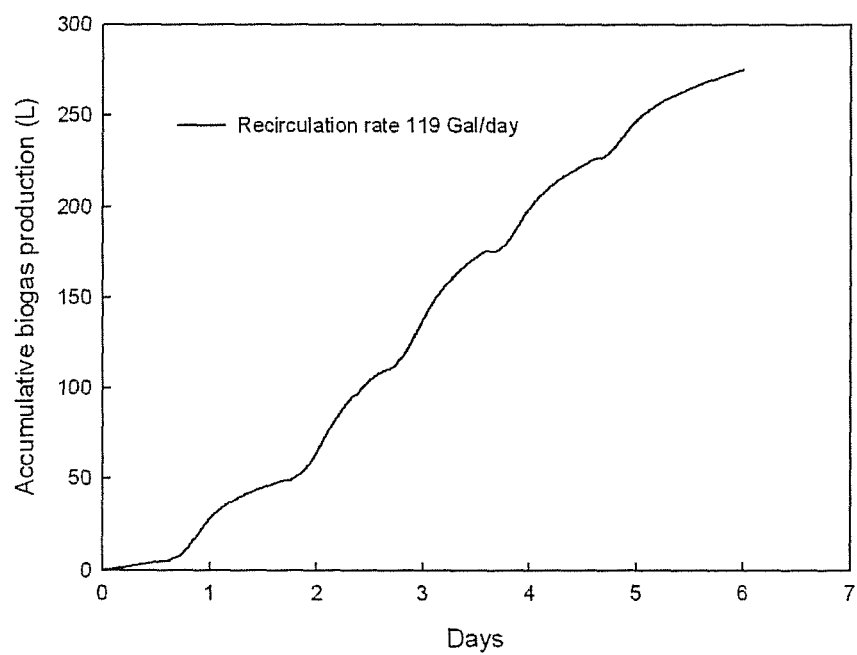
FIG. 9 shows cumulative biogas production at a feeding rate of 10 gal/day in the UASB seed reactor.

FIG. 9 also shows cumulative biogas production in the UASB seed reactor when the feed rate of leachate from the high solids digester is set at 10 gal/day (increased from an initial load rate of 10 gal/week) and the recirculation rate is 119 gal/day. The cumulative biogas production displayed a linear increase, indicating that high loading rate in the UASB seed reactor can be used to improve biogas production.

Figure 10:
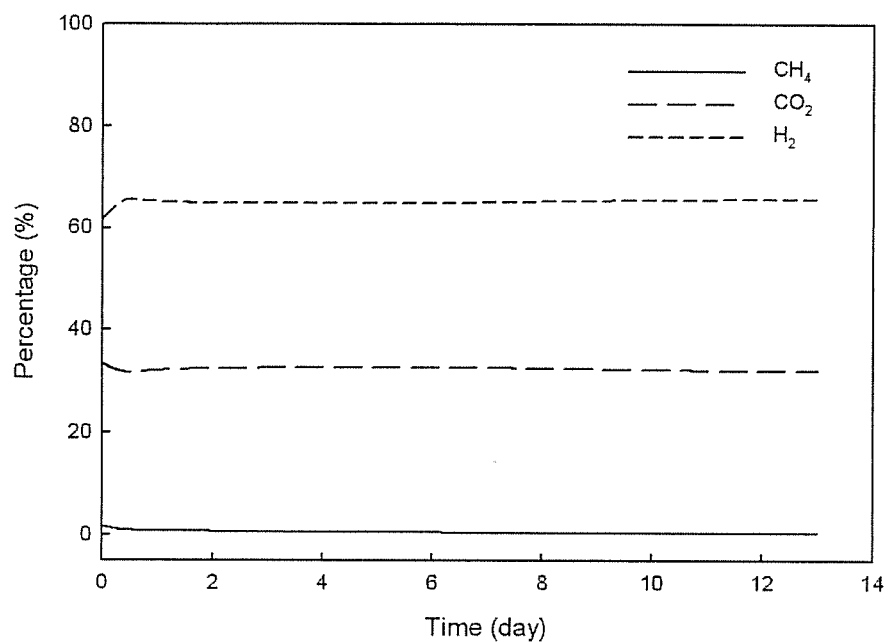
FIG. 10 shows a prediction of $CH_4$, $CO_2$, and $H_2$ in the upper portion of the HSAD reactor recycling effluent without methanogenic seeds.
Figure 11:
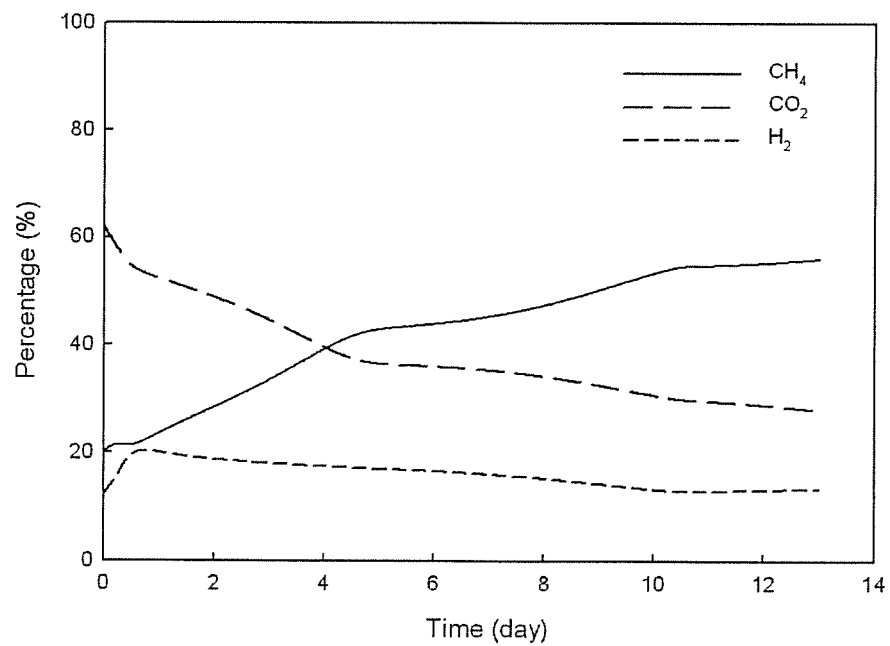
FIG. 11 shows a prediction of $CH_4$, $CO_2$, and $H_2$ in the lower portion of the HSAD reactor recycling effluent without methanogenic seeds.
Figure 12:
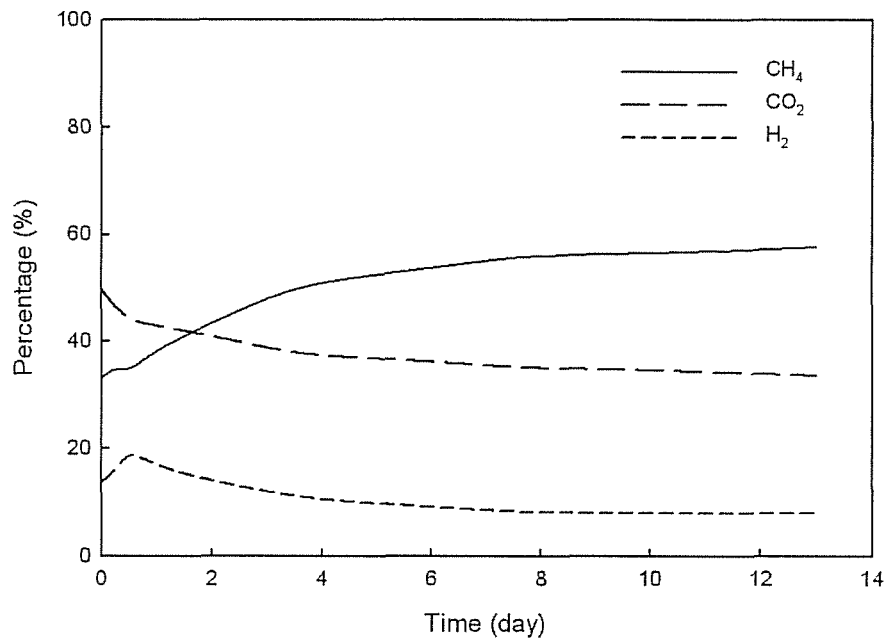
FIG. 12 shows a prediction of $CH_4$, $CO_2$, and $H_2$ in the upper portion of the up-flow anaerobic sludge beds (UASB) seed reactor recycling effluent without methanogenic seeds.
Figure 13:
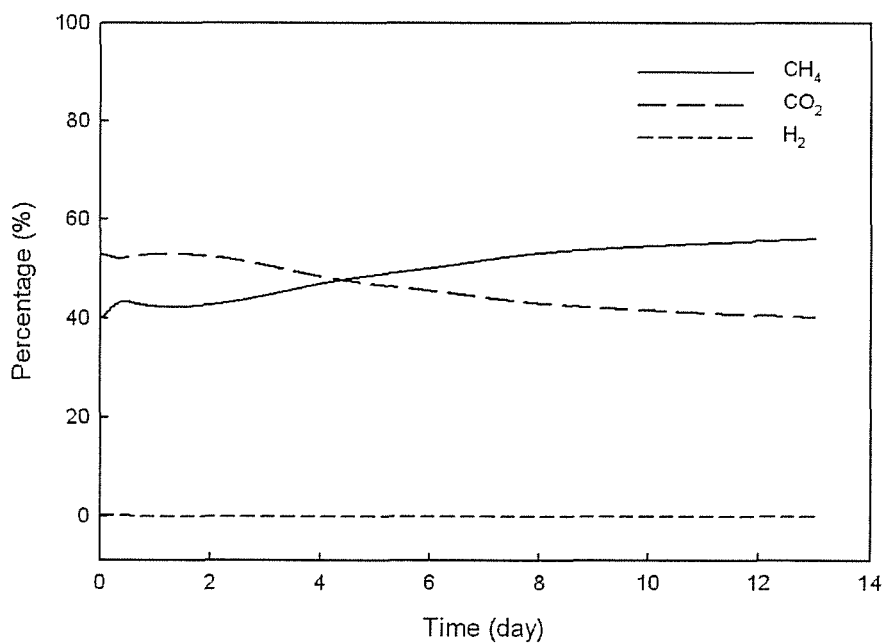
FIG. 13 shows a prediction of $CH_4$, $CO_2$, and $H_2$ in the upper portion of the HSAD reactor recycling effluent with methanogenic seeds.
Figure 14:
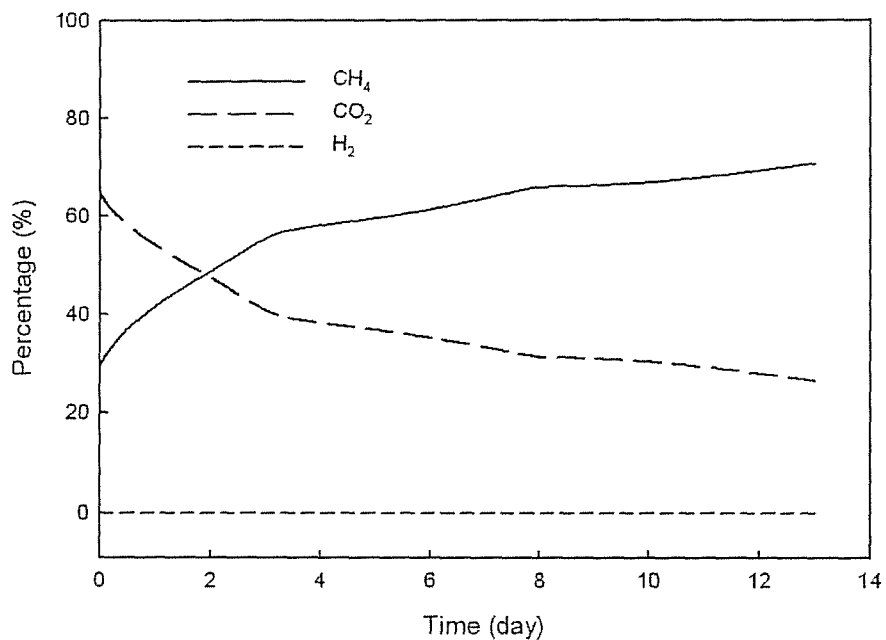
FIG. 14 shows a prediction of $CH_4$, $CO_2$, and $H_2$ in the lower portion of the HSAD reactor recycling effluent with methanogenic seeds
Figure 15:
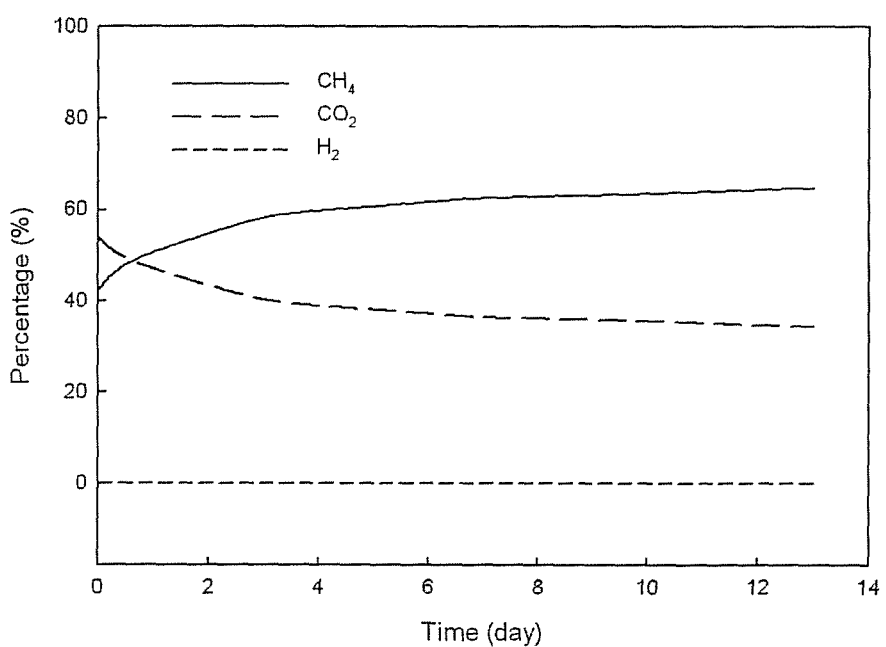
FIG. 15 shows a prediction of $CH_4$, $CO_2$, and $H_2$ in the upper portion of the UASB seed reactor recycling effluent with methanogenic seeds

5. Effect of Recycled Methanogenic Seeds on Methane Concentration in the HADRS System One feature of the present technology is the recycling of methanogenic seeds from the UASB seed reactor to the HSAD reactor. However, it is difficult to separate methanogenic bacteria from the other microorganisms in the reaction mixture in order to test their effect on methane concentration in the HADRS system. Therefore, computer simulation of an anaerobic digestion model No.1 (ADM1) was created to describe this two-stage and two-phase system. Two different conditions were simulated. One was recycling effluent that did not contain methanogenic bacteria from the UASB seed reactor to the HSAD reactor. The other was recycling effluent containing methanogenic bacteria from the UASB seed reactor to the HSAD reactor. The recycling rate was set at 90 L/day and the loading rate was set at 15 kg COD/m³/d. FIG. 10, FIG. 11 and FIG. 12 show the predicted biogas content produced by a system without methanogenic seeds. As can be seen in FIG. 10, a high content (about 65%) of hydrogen was predicted to be produced in the upper portion of the HSAD reactor while methane content was close to 0. Even in the UASB seed reactor, hydrogen still was not predicted to be completely converted into methane, presumably because of the high loading rate and the short hydrolytic retention time. FIG. 13, FIG. 14 and FIG. 15 show the biogas volumes produced by a system with methanogenic seeds (4.87% acetic acid degrading organisms and hydrogen degrading organisms). As can be seen, no hydrogen is predicted to be produced even in the upper portion of the HSAD reactor. The predicted biogas had a high methane content (about 60%) in the HADRS system.

This exercise showed that recycling methanogenic seeds can enhance the preferential production of methane instead of hydrogen in the HSAD reactor, which supports the system design

REFERENCES

1. Parkin, G. F., *Fundamentals of anaerobic-digestion of waste-water sludges*. Journal of Environmental Engineering—ASCE, 1986. 112(5): p. 867-920.
2. Bolzonella, D., F. Fatone, P. Pavan, and F. Cecchi, *Anaerobic fermentation of organic municipal solid wastes for the production of soluble organic compounds*. Industrial & Engineering Chemistry Research, 2005. 44(10): p. 3412-3418.
3. Castillo, E. F., D. E. Cristancho, and V. Arellano, *Study of the operational conditions for anaerobic digestion of urban solid wastes*. Waste Management, 2006. 26(5): p. 546-556.
4. Kalogo, Y. and W. Verstraete, *Technical feasibility of the treatment of domestic wastewater by a ceps-uasb system*. Environmental Technology, 2000. 21(1): p. 55-65.
5. Lew, B., S. Tarre, M. Belavski, and M. Green, *Uasb reactor for domestic wastewater treatment at low temperatures: A comparison between a classical uasb and hybrid uasb-filter reactor*. Water Science and Technology, 2004. 49(11-12): p. 295-301.
6. Al-Jamal, W. and N. Mahmoud, *Community onsite treatment of cold strong sewage in a uasb-septic tank*. Bioresource Technology, 2009. 100(3): p. 1061-1068.
7. Seghezzo, L., G. Zeeman, J. B. van Lier, H. V. M. Hamelers, and G. Lettinga, *A review: The anaerobic treatment of sewage in uasb and egsb reactors*. Bioresource Technology, 1998. 65(3): p. 175-190.

The complete contents of all references cited herein, including patents and patent applications, are hereby incorporated by reference in entirety.

The foregoing Examples describe exemplary embodiments of the invention but should not be interpreted as limiting the invention in any way.

The invention claimed is:

1. A method of producing biogas, comprising the steps of
i) in a first reactor, culturing at least one anaerobic microbial consortium in a high solids medium comprising 10 to 20% solids and having a pH in the range of from 6.0 to 7.5, for a period of time sufficient to produce biogas containing methane and to form a high solids phase and a low solids phase within said first reactor, wherein a) said high solids phase is positioned within a top portion of said first reactor and floats directly on said low solids phase, and wherein oxygen tolerant microorganisms within said high solids phase hydrolyze and produce VFAs from biodegradable solids, and
b) said low solids phase is positioned beneath said high solids phase within a bottom portion of said first reactor, wherein microbial populations within said low solids phase perform anaerobic processes that produce biogases;

and wherein said high solids phase and said low solids phase are in direct contact with each other;

ii) culturing, in a second reactor, at least one methanogen-rich anaerobic culture in a low solids medium comprising at most 1% solids and having a pH in the range of from 6.5 to 8.5, for a period of time sufficient to generate methane;

iii) during one or both of step i) of culturing and step ii) of culturing, removing effluent containing volatile fatty acids (VFAs) from said low solids phase in said first reactor at a rate that is sufficient to at least partially offset a decrease in pH within said high solids phase;

iv) transferring effluent removed from said low solids phase in said first reactor to said second reactor;

v) removing effluent from said low solids medium in said second reactor;

vi) transferring effluent removed from said second reactor to said first reactor at a rate that is sufficient to at least partially offset said decrease in pH within said high solids phase; and vii) recovering biogas produced in at least one of said first and second reactors.

2. The method of claim 1, further comprising a step of processing, in a buffer tank, said effluent removed from said first reactor prior to said step iv) of transferring.

3. The method of claim 2, wherein said step of processing includes adjusting a pH of said effluent by alkalinization.

4. The method of claim 1, wherein said effluent transferred from said low solids medium in said second reactor to said first reactor comprises anaerobic seeds.

5. The method of claim 4, wherein said anaerobic seeds include methanogenic seeds.

6. The method of claim 1, wherein said high solids medium comprises organic municipal solid waste.

7. The method of claim 1, wherein said steps of i) culturing and ii) culturing are performed simultaneously.

8. The method of claim 1, further comprising a step of transferring $H_2$ and $CO_2$ produced in said first reactor to said second reactor.

9. The method of claim 1, wherein said biogas recovered in said recovering step includes methane.

10. The method of claim 1, further comprising the step of i) recovering nutrients from said effluent removed from said second reactor prior to said step vi) of transferring.

11. The method of claim 1, further comprising the steps of
i) transferring effluent from said first reactor and/or said second reactor to a buffer tank;
ii) recovering nutrients from said effluent transferred to said buffer tank; and
iii) transferring nutrient depleted effluent from said buffer tank to said first reactor.

12. The method of claim 1, further comprising a step of mixing said high solids phase.

13. The method of claim 12, wherein said step of mixing is performed by one or more of: i) mechanical mixing; ii)

introducing effluent from said second reactor into said top portion of said first reactor; and iii) upward movement of biogas.

14. The method of claim 1 wherein said vi) transferring step transfers anaerobic seeds from said second reactor to said first reactor.

15. The method of claim 14, wherein said anaerobic seeds include methanogenic seeds.

16. The method of claim 1 wherein said iv) transferring step transfers effluent from a low solids phase positioned within a bottom portion of said first reactor to said second reactor.

17. The method of claim 1, wherein said high solids phase comprises from about 15 to about 50% solids.

18. The method of claim 1, wherein said low solids phase comprises from about 0 to about 5% solids.

19. The method of claim 1, wherein an oxygen concentration of said high solids phase is higher than an oxygen concentration of said low solids phase.

20. The method of claim 13, wherein said mechanical mixing is intermittent.

* * * * *